United States Patent [19]

Martinez et al.

[11] Patent Number: 5,589,357
[45] Date of Patent: Dec. 31, 1996

[54] MILK PROTEIN PARTIAL HYDROLYSATE AND PROCESS FOR PREPARATION THEREOF

[75] Inventors: Sarah B. Martinez; H. Lee Leary, Jr.; Debra J. Nichols, all of Evansville, Ind.

[73] Assignee: Bristol-Myers Squibb Company, Princeton, N.J.

[21] Appl. No.: 342,977

[22] Filed: Nov. 21, 1994

Related U.S. Application Data

[62] Division of Ser. No. 85,213, Jun. 30, 1993.

[51] Int. Cl.⁶ ........................................ C12P 21/06
[52] U.S. Cl. .................. 435/68.1; 426/580; 426/588; 426/656; 426/657; 426/801
[58] Field of Search .................. 435/68.1; 426/580, 426/558, 656, 657, 801

[56] References Cited

U.S. PATENT DOCUMENTS

| | | | |
|---|---|---|---|
| 4,293,571 | 10/1981 | Olofsson et al. | 426/7 |
| 4,981,704 | 1/1991 | Thibault | 426/41 |
| 5,039,532 | 8/1991 | Jost et al. | 435/68.1 |
| 5,405,637 | 4/1995 | Martinez et al. | 426/580 |

*Primary Examiner*—Herbert J. Lilling
*Attorney, Agent, or Firm*—Thomas R. Savitsky

[57] ABSTRACT

Disclosed is a milk protein partial hydrolysate prepared by enzymatic hydrolysis and infant formula prepared therefrom. The hydrolysate has reduced antigenicity and is prepared from a mixture of whey protein and casein wherein the degree of hydrolysis is between 4 and 10%.

6 Claims, No Drawings

MILK PROTEIN PARTIAL HYDROLYSATE AND PROCESS FOR PREPARATION THEREOF

CROSS REFERENCE TO RELATED APPLICATION

This application is a divisional of application Ser. No. 08/085,213 filed Jun. 30, 1993.

FIELD OF THE INVENTION

The present invention relates to a process for the enzymatic preparation of a milk protein partial hydrolysate and infant formula products of reduced antigenicity containing said hydrolysate.

BACKGROUND OF THE INVENTION

A large number of infant formulas are based on proteins from cow's milk. Infants who are truly allergic to milk protein require infant formulas wherein the proteins are extensively hydrolyzed to contain a minimum of residual molecular structures. For non-allergic infants, an infant formula with reduced antigenicity has prophylactic benefits in that it can delay or prevent sensitization which could otherwise lead to clinical symptoms of allergy. The allergenic potential of cow milk-protein based formulas can be reduced by protein hydrolysis.

To ideally meet the composition of human milk, the cow milk protein in infant formulas should contain both whey protein and casein in an appropriate ratio. While a number of products based on intact milk protein meet a desirable whey protein to casein ratio, almost all of the commercially available partially hydrolyzed formulas are based on 100% whey protein.

processes for preparation of partial hydrolysates described in the literature generally involve multi-step hydrolysis and physical separations after the hydrolysis to eliminate enzymes and/or residual proteins. Most processes also involve constant pH control during hydrolysis. Also, unless another process step is introduced, the resulting hydrolysate will usually have a high level of salts which can pose formulation problems in the infant formula, the level of minerals of which are usually regulated at a certain level.

U.S. Pat. No. 5,039,532 describes two steps of enzymatic hydrolysis to attain a hydrolysate of desired characteristics. It also describes preparation of an infant formula which is ultra-high temperature (UHT) sterilized. U.S. Pat. Nos. 4,293,571 and 4,981,704 both describe partial hydrolysates prepared using pancreatic enzymes which involve post-hydrolysis membrane processes to separate out the residual proteins and enzymes.

A common characteristic of protein hydrolysates, particularly hydrolysates containing casein, is bitter flavor development putatively due to liberation of peptides with hydrophobic end groups. Moreover, the emulsifying property of proteins generally is also decreased as the degree of hydrolysis increases. Japanese Patent 1160458 describes a milk protein hydrolysate (5–20% hydrolyzed) which is surface active and shows emulsifying activity in foods such as ice cream and whipping cream. However, in products such as liquid infant formulas which undergo sterilization processes, further denaturation of the protein hydrolysate renders it less functional in an emulsion. This is manifested in the product as a separation into a serum and cream layer. The high temperature-short time conditions of UHT sterilization is commonly preferred to conventional retort sterilization to prevent the adverse exposure to heat.

Thus, it would be highly desirable to have a partial protein hydrolysate which has reduced antigenicity, has a whey protein to casein ratio which provides a protein composition similar to human milk, has improved taste, and/or has improved emulsifying activity.

SUMMARY OF THE INVENTION

The present invention is directed to a partial hydrolysate of a protein mixture wherein said protein mixture comprises whey protein and casein and wherein the hydrolysate has a degree of hydrolysis between 4 and 10% and to an infant formula containing said partial hydrolysate.

The present invention is also directed to a process for preparing a partial hydrolysate of a protein mixture comprising contacting a mixture of whey protein and casein with an enzyme mixture comprising at least 1800 USP Trypsin Units/mg and at least 350 USP Chymotrypsin Units/mg in an aqueous suspension under conditions to result in a degree of hydrolysis between 4 and 10%.

DETAILED DESCRIPTION OF THE INVENTION

The present invention provides a partial hydrolysate of a mixture of whey proteins and casein which is appropriate to the production of nutritional products of reduced antigenicity, as well as a process for its preparation. The partial hydrolysate of the invention also is closer to the whey/casein protein ratio of human milk as compared to prior art partial protein hydrolysates. Additionally, the partial hydrolysate of the invention preferably has improved taste and improved emulsifying activity.

The process according to the invention may be carried out by using starting materials consisting of mixtures of whey protein and casein preferably in ratios similar to that found in human milk. Preferably the protein mixture comprises about 60 to about 80% whey protein and about 40 to about 20 % casein more preferably is about 40 to about 60% whey protein and about 60 to about 40% casein. Percentages of casein and whey protein are expressed on a weight basis. The whey proteins may be sourced from a whey obtained from cheese making, particularly a sweet whey such as that resulting from the coagulation of casein by rennet. The whey proteins may also be used in the form of concentrates in the range of about 35–80% protein as obtained by ultrafiltration (UF whey). This whey material, optionally, may also be demineralized by ion exchange and/or electrodialysis (ED whey). The casein source can either be acid casein or non-fat milk solids (NFDM). The whey protein and casein can be used either in the form of liquid concentrates or powders. For the process of this invention, the proteins are diluted or reconstituted to solutions containing about 10 to about 60 g protein per liter, preferably about 40 to about 60 g protein per liter.

For the process of the present invention, a mixture of trypsin and chymotrypsin, the enzymatic specificities of which are complementary, is used. The enzyme mixture preferably is free of other contaminating proteases such as carboxypeptidase A and B or leucine aminopeptidase. The trypsin in the mixture has equal to or greater than 800 USP units/mg, preferably equal to or greater than 1000 USP units/mg, and more preferably equal to or greater than 1800 USP units/mg. One USP Trypsin Unit is the activity causing a change in absorbance of 0.003 per minute under the conditions of 5 minutes assay time, pH 7.6, 25±0.1° C. and N-benzoyl-L-arginine ethyl ester hydrochloride (BAEE) as substrate.

The chymotrypsin in the mixture has equal to or greater than 150 USP units/mg, preferably equal to or greater than 200 USP units/mg more preferably equal to or greater than 350 USP units/mg. One USP Chymotrypsin Unit is the activity causing a change in absorbance of 0.0075 per minute under the conditions shown under the conditions of 5 minutes assay time, pH 7.6, 25 0.1° C. with N-acetyl-L-tyrosine ethyl ester (ATEE) as substrate.

Commercial sources of enzymes suitable for use in the present invention include Novo Nordisk Bioindustrials, Inc., Danbury, Conn., U.S.A., (particularly PEM 2500S), Enzyme Development Corp., New York, N.Y., U.S.A., Intergen Company, purchase, N.Y., U.S.A., and Scientific Protein labs., Waunakee, Wis., U.S.A.

TO obtain a hydrolysate of desirable properties, it is typically necessary that the mixture of trypsin and chymotrypsin have a trypsin to chymotrypsin ratio of about 1.3 to about 18 in the USP units described above, preferably about 1.3 to about 10, and more preferably about 4 to about 6. For the purpose of the invention, the enzyme mixture typically is used at levels of about 0.4% to about 1.2% by weight of the total protein being hydrolyzed, preferably about 0.6% to about 0.8% by weight.

An optional preliminary step prior to hydrolysis is preheating of the protein solution to insure denaturation of whey protein fractions e.g., serum albumin (BSA) and immunoglobulins (particularly IgG). This step usually results in a diminished residual antigenicity when assessed immunochemically (as described hereinafter). The pretreatment step is typically performed by heating to about 75° C. to about 85° C. for about 10 minutes to about 30 minutes. The hydrolysis itself is typically conducted at temperatures of about 30° C. to about 50° C. for about 2 to about 6hours, the lower temperature limit corresponding to the upper time limit and vice versa. Maintenance of pH typically is not required during hydrolysis, since the hydrolysis usually proceeds at pH 6.5–6.8 without additional pH control. The pH should be kept within the range of about 6.5 to 8.0, with or without pH control.

Irrespective of the conditions of the hydrolysis, the hydrolysate preferably is subjected to an additional step of enzyme inactivation. This enzyme inactivation can be a heat treatment which comprises heating to a temperature of about 85° C. for about 10 minutes. Alternatively, the enzyme may be inactivated by sterilization at ultra-high temperature (e.g., about 130° C. for about 45 seconds) after which the product can be stored in a liquid state. The hydrolysate may also be concentrated by evaporation or dried by spray drying.

To monitor the degree of hydrolysis, the United States Pharmacopeia (USP) formol titration method is used wherein the increase in free amino groups during the hydrolysis of peptide bonds can be estimated by titration with sodium hydroxide. The degree of hydrolysis is between 4% and 10%, preferably between 5% and 7%. It is an advantage of the present invention that the degree of hydrolysis is lower than achieved in certain prior art processes; yet a significant reduction in antigenicity is still obtained.

Size exclusion chromatography (SEC) is used for determination of hydrolysate peptide molecular weight distribution. The peptides in the hydrolysate are separated according to molecular size in a TSK G-2000 SWXL column maintained at 37° C. and eluted at 0.7 ml/minute with TFA and acetonitrile in KCl. Absorption at 214 nm vs. retention time is generated with a UV detector and compared with those of standard proteins and peptides of known molecular weight. The partial hydrolysate of the invention preferably has an average molecular weight of 2,000, a maximum molecular weight of 19,000 and is comprised of peptides with the following distribution, as a function of their molar mass:

| Molar Mass (g per mole) | % Molecular Weight Distribution |
| --- | --- |
| MM > 5000 | 8.2 |
| 5000 > MM > 3000 | 14.5 |
| 3000 > MM > 2000 | 15.8 |
| 2000 > MM > 1000 | 26.2 |
| 1000 > MM > 500 | 17.8 |
| MM > 500 | 17.5 |

The hydrolysate of the invention is preferably devoid of detectable intact milk protein. The absence of intact milk protein in the hydrolysate is demonstrated in sodium dodecylsulfate-polyacrylamide gel electrophoresis (SDS-PAGE). SDS-PAGE is performed with a 4 to 20% Tris-glycine gradient gel. Fifteen micrograms of hydrolyzed protein is treated with SDS, reduced with 2-mercaptoethanol, heated and applied to individual lanes. At the completion of the electrophoretic separation, the gel is silver stained to reveal residual peptides. Direct comparisons are made in the same gel using 5 micrograms of the non-hydrolyzed protein starting material.

The residual antigenicity of the hydrolysate is determined using an enzyme-linked immunosorbent assay (ELISA). Non-hydrolyzed milk protein is immobilized on a solid phase at concentrations that fall within the linear dose response range established in the assay. Hydrolysate preparations are similarly immobilized. Subsequent, sequential incubations with rabbit anti-cow milk protein and an enzyme conjugate reactive with rabbit IgG reveals the presence of antigenically recognizable protein and peptides. Results obtained with the hydrolysate are compared on a mass basis to those obtained with the non-hydrolyzed protein starting material. The percent antigenicity reduction of the hydrolysate is then calculated. The hydrolysate of the invention has a reduction in antigenicity of at least about 80%, preferably at least about 85%, more preferably at least about 90%, and most preferably at least about 95%.

The hydrolysate from the invention is suitable for use in an infant formula, processed by conventional unit operations commonly used in the food industry. The reduction in antigenicity of such formulas as compared to the corresponding non-hydrolyzed protein is determined by the ELISA method described above.

An infant formula of the invention made with the hydrolysate of the invention has a reduction in antigenicity of at least about 80%, preferably at least about 85%, more preferably at least about 90%, and most preferably at least about 95%, relative to a corresponding non-hydrolyzed protein mixture. The infant formula of the invention can be in the form of a powder, concentrated liquid, or ready-to-use liquid.

In addition, the infant formula of the invention has an improved taste relative to a corresponding formula made with partially hydrolyzed whey protein.

The infant formula of the invention contains ingredients which are designed to meet the nutritional needs of the human infant. Thus, in addition to the partial protein hydrolysate of the invention, a typical infant formula will contain a lipid source, a carbohydrate source and other nutrients such as vitamins and minerals. Typically, animal oils, vegetable oils, starch, sucrose, lactose and/or corn syrup solids will be added to the formula to supply part or all of the above nutrients.

It is preferred that the infant formula of the invention is nutritionally complete. By the term "nutritionally complete" is meant that the composition contains adequate nutrients to sustain healthy human life for extended periods.

The amount of partial protein hydrolysate per 100 kcal of total formula is typically about 1.8 g to about 4.5 g; the amount of lipid source per 100 kcal of total formula is typically about 3.3 g to about 6 g; and the amount of carbohydrate source per 100 kcal of total formula is typically about 7 g to about 14 g.

The carbohydrate source in the infant formula can be any suitable carbohydrate known in the art to be suitable for use in infant formulas. Typical carbohydrate sources include sucrose, fructose, glucose, maltodextrin, lactose, corn syrup, corn syrup solids, rice syrup solids, rice starch, modified corn starch, modified tapioca starch, rice flour, soy flour, and the like.

The lipid source in the infant formula can be any lipid or fat known in the art to be suitable for use in infant formulas. Typical lipid sources include milk fat, safflower oil, egg yolk lipid, olive oil, coconut oil, palm oil, palm kernel oil, soybean oil, sunflower oil, fish oil and fractions derived thereof such as palm olein, medium chain triglycerides (MCT), and esters of fatty acids wherein the fatty acids are, for example, arachidonic acid, linoleic acid, palmitic acid, stearic acid, docosahexaeonic acid, eicosapentaenoic acid, linolenic acid, oleic acid, lauric acid, capric acid, caprylic acid, caproic acid, and the like. High oleic forms of various oils are also contemplated to be useful herein such as high oleic sunflower oil and high oleic safflower oil. Medium chain triglycerides contain higher concentrations of caprylic and capric acid than typically found in conventional oils, e.g., approximately three-fourths of the total fatty acid content is caprylic acid and one-fourth is capric acid.

The infant formula containing the partial protein hydrolysate of the invention optionally may be supplemented with various free amino acids to provide a nutritionally balanced amino acid content. Examples of such free amino acids include L-tryptophan, L-methionine, L-cystine, L-tyrosine, and L-arginine.

Nutritionally complete compositions contain all vitamins and minerals understood to be essential in the daily diet and these should be present in nutritionally significant amounts. Those skilled in the art appreciate that minimum requirements have been established for certain vitamins and minerals that are known to be necessary for normal physiological function. Practitioners also understand that appropriate additional amounts (overages) of vitamin and mineral ingredients need to be provided to compensate for some loss during processing and storage of such compositions.

To select a specific vitamin or mineral compound to be used in the infant formula requires consideration of that compound's chemical nature regarding compatibility with the processing and shelf storage.

Examples of minerals, vitamins and other nutrients optionally present in the composition of the invention include vitamin A, vitamin $B_e$, vitamin $B_{12}$, vitamin E, vitamin K, vitamin C, folic acid, thiamine, inositol, riboflavin, niacin, biotin, pantothenic acid, choline, calcium, phosphorous, iodine, iron, magnesium, copper, zinc, manganese, chloride, potassium, sodium, selenium, chromium, molybdenum, taurine, and L-carnitine. Minerals are usually added in salt form. In addition to compatibility and stability considerations, the presence and amounts of specific minerals and other vitamins will vary somewhat depending on the intended infant population.

The infant formula of the invention also typically contains emulsifiers and stabilizers such as soy lecithin, carrageenan, and the like.

The infant formula of the invention may optionally contain other substances which may have a beneficial effect such as lactoferrin, nucleotides, nucleosides, immunoglobulins, and the like.

The osmolality of the liquid infant formula of the invention (when ready to consume) is typically about 100 to about 500 mOsm/kg $H_2O$, 1 more typically about 200 to about 400 mOsm/kg $H_2O$.

The infant formula of the invention can be sterilized, if desired, by techniques known in the art, for example, heat treatment such as autoclaving or retorting, and the like.

The infant formula of the invention can be packaged in any type of container known in the art to be used for storing nutritional products such as glass, lined paperboard, plastic, coated metal cans and the like.

The following examples are to illustrate the invention but should not be interpreted as a limitation thereon.

EXAMPLE 1

The proteins are solubilized at 50° C. at concentrations of 4–6% protein. This corresponds to 10–25% solids depending on the type of protein used. The preheat treatment constitutes holding at 75° C. for 30 minutes. The mixture is cooled back to 50° C. and the enzyme mixture is added. The hydrolysis can be conducted over a temperature range of 30–50° C. for 2–6 hours. The hydrolysis time and temperature are interrelated, the lower temperature limit corresponding to the upper time limit and vice versa. The pH of the mixture may or may not be controlled during the hydrolysis period. To inactivate the enzyme, the hydrolysate is subjected to steam injection temperatures of 130° C. for 45 seconds. This high temperature step together with the preheat treatment and enzyme hydrolysis yields a hydrolysate of reduced antigenicity. The pH is adjusted to at least 6.6, if necessary, with potassium hydroxide to prevent heat coagulation during the heat treatment.

EXAMPLE 2

A procedure as in Example 1 was performed but with a pH adjustment to 7.5 with KOH before a preheat treatment of 85° C. for 10 minutes. To inactivate the enzyme, the partial hydrolysate is heated to 85° C. for 10 minutes. As in Example 1, pH is adjusted to at least 6.6 before the latter step.

Different process variables are shown in the following table to illustrate preparation of hydrolysates according to Examples 1 and 2. In all cases the weight ratio of whey protein:casein was 80:20.

| VARIABLE | PROCESS EXAMPLE | % D.H. | % REDUCTION IN ANTIGENICITY (HYDROLYSATE) |
|---|---|---|---|
| Trypsin to chymotrypsin ratio | | | |
| 1.3 | 2 | 6.77 | 92.5 |
| 5.3 | 2 | 6.50 | 94.3 |
| 8.8 | 2 | 7.24 | 93.7 |

-continued

| VARIABLE | PROCESS EXAMPLE | % D.H. | % REDUCTION IN ANTIGENICITY (HYDROLYSATE) |
|---|---|---|---|
| Enzyme concentration (% of Protein) | | | |
| 0.8 | 2 | 5.50 | 92.7 |
| 0.6 | 2 | 4.88 | 91.3 |
| 0.4 | 2 | 4.72 | 91.3 |
| Hydrolysis time (Hrs.) | | | |
| 2 | 1 | 4.53 | 90.6 |
| 2 | 2 | 4.55 | 91.8 |
| 3 | 1 | 4.57 | 92.4 |
| 3 | 2 | 5.48 | 93.9 |
| 4 | 1 | 5.35 | 92.4 |
| 4 | 2 | 6.50 | 94.3 |
| 6 | 2 | 6.73 | 94.6 |
| Hydrolysis temperature (°C.) | | | |
| 30 | 2 | 4.58 | 89.9 |
| 40 | 2 | 5.71 | 91.6 |
| 50 | 2 | 5.76 | 94.6 |

EXAMPLE 3

For a liquid infant formula, to the partial hydrolysate from Example 1, is added lactose and minerals dissolved beforehand. The mixture is heated to 70° C. in a plate type heat exchanger. This is followed by the introduction of fats which consists of palm olein, sunflower oil, coconut oil, soy oil, lecithin, mono-and diglycerides and fat soluble vitamins. The oils are melted before addition to the mixture. After preheating to about 75° C., the mixture is heated to 140° C. for 45 seconds by direct injection of steam and cooled to 70° C. by a plate cooler. This is then followed by homogenization in two stages, first at 175 bar and then at 35 bar. The mixture is then cooled to 5–7° C. with a plate cooler and stored in an intermediate storage tank where water soluble vitamins are added. The bulk product from this process has a heat coagulation time of more than 30 minutes. The product is sterilized in conventional retort systems.

| Peptides | 1.65% |
|---|---|
| Fat | 3.60% |
| Carbohydrates | 6.52% |
| Minerals | 0.48% |
| Vitamins | Trace |

EXAMPLE 4

For another liquid infant formula, a procedure as in Example 3 and partial hydrolysate from Example 2, except that direct steam injection temperature is 121° C. and the liquid is sterilized at 145° C. for 4.97 seconds and aseptically packed in containers. Composition is the same as in Example 3

EXAMPLE 5

For an infant formula powder, a procedure as in Example 3 with a partial hydrolysate from either Example 1 or 2, except that the product is not subjected to steam injection temperatures before a 2-stage homogenization step of 125 bar and 50 bar. The powder base can be evaporated to 50% solids before spray drying.

| Peptides | 13.1% |
|---|---|
| Fat | 28.6% |
| Carbohydrates | 51.8% |
| Minerals | 3.8% |
| Vitamins | 0.2% |
| Moisture | 2.5% |

Infant formulas produced according to processes in Examples 1 to 5 demonstrate reduced antigenicity as shown in the following table.

| PRODUCT FORM (Whey protein:casein weight ratio. Protein Source) | PROCESS EXAMPLE | % REDUCTION IN ANTIGENICITY |
|---|---|---|
| Liquid (80:20. UF* whey, NFDM**) | Examples 1, 4 | 92.4 |
| Liquid (80:20. UF whey, NFDM) | Examples 2, 4 | 94.3 |
| Liquid (80:20. UF whey, NFDM) | Examples 1, 3 | 92.1 |
| Liquid (80:20. UF whey, casein) | Examples 1, 4 | 81.4 |
| Liquid (60:40. UF whey, NFDM) | Examples 1, 4 | 87.8 |
| Liquid (60:40. ED*** whey, NFDM) | Examples 1, 4 | 94.6 |
| Powder (80:20. UF whey, NFDM) | Examples 2, 5 | 92.3 |

*UF = ultrafiltered
**NFDM = non-fat dried milk
***ED = electrodialyzed

EXAMPLE 6

A 40-member consumer panel evaluates and compares a formula of the invention substantially as described in Example 4 to a commercial formula (Good Start™ Iron Fortified Infant Formula, available from Carnation Company, Glendale, Calif., USA) having similar ingredients except that the protein component is partially hydrolyzed 100% whey protein. Samples are served at room temperature and evaluated by the panel. Specific and sensory attributes of the infant formula such as bitterness, aftertaste, mouthfeel, as well as overall flavor score, are compared using a 9-point hedonic scale (9=like extremely, 1=dislike extremely). The results are in the following table.

| | Formula of the Invention | Good Start |
|---|---|---|
| Appearance | 7.3 | 6.7 * |
| Flavor | 4.0 | 3.3 * |
| Flavor Strength | 4.5 | 4.0 |
| Sweetness | 4.8 | 4.1 * |
| Milky | 5.4 | 5.1 |
| Buttery | 5.0 | 4.5 |
| Meaty | 4.4 | 4.1 |
| Bitter | 3.6 | 3.6 |
| Aftertaste | 3.0 | 3.7 |
| Overall | 4.2 | 3.6 * |
| Preference | 68% | 32% * |
| Comments | Bitter 8% Poor Color 8% | Bitter 18% |

*Indicate significant difference between samples at 95% confidence level.

The formula of the invention is significantly preferred over Good Start. Panelists' comments indicated that the bitter nature of Good Start is the primary reason for the preference of the formula of the invention over Good Start.

The invention has been described in detail with particular reference to preferred embodiments thereof, but it will be understood that variations and modifications can be effected within the spirit and scope of the invention.

We claim:

1. A process for preparing a partial hydrolysate of a protein mixture comprising whey protein and casein, said process comprising:

(a) performing a pretreatment step comprising heating the protein mixture at about 75° C. to about 85° C. for about 10 minutes to about 30 minutes;

(b) contacting the protein mixture resulting from step (a) with an enzyme mixture comprising at least 1800 USP Trypsin Units/mg and at least 350 USP Chymotrypsin Units/mg in an aqueous suspension wherein the ratio in USP units of Trypsin to Chymotrypsin is about 1.3 to about 18, at a temperature of about 30° C. to about 50° C., a pH of about 6.5 to about 8.0, for about 2 to about 6 hours, and;

(c) inactivating the enzyme mixture.

2. The process of claim 1 wherein the ratio in USP units of Trypsin to Chymotrypsin is about 1.3 to about 10.

3. The process of claim 1 wherein the ratio in USP units of Trypsin to Chymotrypsin is about 4 to about 6.

4. The process of claim 1 wherein the amount of enzyme mixture is between about 0.4 and about 1.2%, based on the weight of the protein in the mixture.

5. The process of claim 1 wherein the enzyme mixture is inactivated by heating to about 85° C. for about 10 minutes or 130° C. for about 45 seconds.

6. The process of claim 5 followed by the additional step of removing water by evaporation or spray drying.

* * * * *